United States Patent
Horrigan et al.

Patent Number: 5,811,043
Date of Patent: Sep. 22, 1998

[54] METHOD OF SOFT TIP FORMING

[75] Inventors: John B. Horrigan, Merrimack; Michael C. Riopel, Ipswich, both of Mass.

[73] Assignee: Medtronic, Inc., Minneapolis, Minn.

[21] Appl. No.: 724,266

[22] Filed: Sep. 19, 1996

Related U.S. Application Data

[62] Division of Ser. No. 368,186, Jan. 4, 1995, abandoned.

[51] Int. Cl.⁶ ............................ B29C 43/02; B29C 65/02
[52] U.S. Cl. .................... 264/138; 264/230; 264/248; 264/296; 264/319; 156/85; 156/86; 156/304.2; 156/304.6
[58] Field of Search ............................ 264/248, 296, 264/319, 322, 138, 230, DIG. 71; 604/265, 282; 425/383; 156/85, 86, 304.2, 304.6

[56] References Cited

U.S. PATENT DOCUMENTS

| | | | |
|---|---|---|---|
| 4,531,943 | 7/1985 | Van Tassel et al. | 604/280 |
| 4,551,292 | 11/1985 | Fletcher et al. | 264/139 |
| 4,563,181 | 1/1986 | Wijayarathna et al. | 604/280 |
| 4,596,563 | 6/1986 | Pande | 604/264 |
| 4,636,346 | 1/1987 | Gold et al. | 264/139 |
| 4,863,442 | 9/1989 | DeMello et al. | 604/282 |
| 4,886,506 | 12/1989 | Lovgren et al. | 604/280 |
| 4,899,787 | 2/1990 | Ouchi et al. | 138/131 |
| 5,078,702 | 1/1992 | Pomeranz | 604/264 |
| 5,156,792 | 10/1992 | Holdaway et al. | 264/230 |
| 5,160,559 | 11/1992 | Scovil et al. | 156/73.6 |
| 5,163,431 | 11/1992 | Griep | 128/658 |
| 5,221,270 | 6/1993 | Parker | 604/282 |
| 5,234,416 | 8/1993 | Macaulay et al. | 604/282 |
| 5,254,107 | 10/1993 | Soltesz | 604/282 |
| 5,279,596 | 1/1994 | Castaneda et al. | 604/282 |
| 5,354,518 | 10/1994 | Okada et al. | 264/1.25 |
| 5,403,292 | 4/1995 | Ju | 604/282 |
| 5,409,644 | 4/1995 | Martin et al. | 264/322 |
| 5,423,773 | 6/1995 | Jiminez | 604/282 |
| 5,509,910 | 4/1996 | Lunn | 604/282 |
| 5,545,149 | 8/1996 | Brin et al. | 604/265 |

FOREIGN PATENT DOCUMENTS 9215358  9/1992  WIPO.

OTHER PUBLICATIONS

7F Scimed Triguide sample Lite with green transition.

*Primary Examiner*—Jan H. Silbaugh
*Assistant Examiner*—Mark Eashoo
*Attorney, Agent, or Firm*—David S. Brin; Dianne M. F. Plunkett; Harold R. Patton

[57] ABSTRACT

The present invention comprises a catheter method of manufacture. The method includes the provision of a subassembly of a lubricious liner and reinforcement. Over the subassembly, a shaft tube, transition tube, and soft tip tube are placed in an abutting relationship to each other, forming an assembly. A first tube of heat shrink is advanced over the assembly, heat is applied to fuse the assembly, and the first heat shrink is removed. Subsequently, the soft tip of the catheter is shaped using a second tube of heat shrink, which is placed over the distal end of the assembly. Heat is applied to the second heat shrink to cause the tip material to flow and to draw the tip material over the distal end of the lubricious liner. The second heat shrink is removed, completing the catheter manufacture.

12 Claims, 3 Drawing Sheets

METHOD OF SOFT TIP FORMING

This is a divisional of application Ser. No. 08/368,186 filed on Jan. 4, 1995, now abandoned.

FIELD OF THE INVENTION

The present invention relates to catheters, and more particularly, to a method of soft tip attachment.

BACKGROUND OF THE INVENTION

Catheters are tube-like members inserted into the body for diagnostic or therapeutic reasons. One of the therapeutic procedures applicable to the present invention is known as percutaneous transluminal coronary angioplasty (PTCA). This procedure can be used, for example, to reduce arterial build-up of cholesterol fats or atherosclerotic plaque. Catheters must have sufficient stiffness to be pushed through vessels as well as sufficient rigidity to provide a high degree of torsional control. Stiffness or rigidity in the catheter tip poses the danger of puncturing or otherwise damaging a vessel as it twists through the vascular system. It is therefore desirable for catheters to have a soft or flexible distal tip. Examples of such soft tip catheters are known in the art.

The trend toward catheters with larger inside diameters and softer distal tip segments results, however, in a substantially weaker bond between the soft tip and the distal catheter shaft because of the thinner wall thickness and lower tensile strength of the softer materials. The following methods of tip attachment are known in the art.

Soft tips are often attached by means of a lap joint or butt joint at the distal end of the catheter body where the soft tip has been fused or welded to the catheter body. A butt joint or lap joint is undesirable because they create a stress concentration area at the distal end of the catheter shaft in a plane perpendicular to the longitudinal axis of the catheter shaft. The effect of this stress concentration is an low bond strength between the catheter shaft and the soft tip when the wall thickness of the catheter shaft is less than 0.3 mm.

U.S. Pat. No. 4,596,563 to Pande for a "Thin-Walled Multi-Layered Catheter Having a Fuseless Tip" discloses a two layered tubular body having a rigid inner sheath and a flexible outer sheath. The tip portion is fuseless with respect to the rest of the catheter, the tip portion being an integral extension of the flexible outer sheath that is formed over a gap between lengths of the rigid inner sheath.

U.S. Pat. No. 4,636,346 to Gold et al for a "Preparing Guiding Catheter" discloses a three-layered tubular body having a lubricous inner sheath defining a lubricous guiding lumen, a rigid intermediate sheath and a flexible outer sheath. The distal tip portion has a similar construction but from which the rigid intermediate sheath is omitted. Col. 5, lines 12–20 discloses a tip portion that may be an initially separate member affixed to the elongated tubular body 22 by suitable means, such as by heating, by other energy sources, and/or by adhesives or the like. Such assembly can be assisted by the use of a length of shrinkable tubing that is placed over the joint location prior to and during the assembly operation in order to enhance the smoothness and strength of the joint. It is an object of the invention to not require adding any braiding or strands of strengthening material.

U.S. Pat. No. 4,863,442 to DeMello et al for a "Soft Tip Catheter" discloses a tubular body with a wire-braided Teflon® core and a polyurethane jacket. The distal end of the jacket is removed from the core, and a soft polyurethane tip is applied to the core over the region where the jacket has been removed. The tip overlaps the core for approximately two millimeters and extends distally approximately two millimeters beyond the distal end of the core. The tip may be applied to the core as a separate tube bonded to it or be built up on the core by repeatedly dipping the tip in a polyurethane slurry, or be molded onto the distal end of the core. An embodiment at col. 5, lines 30–39 discloses a sleeve of shrink film 64 placed over the polyurethane tube 40 with the distal end of the jacket 18 and overlapping the shoulder 34. With the sleeve of shrink film 64 in place as shown in FIG. 2G, the distal end of the assembly is heated to a temperature and for a time sufficient to cause the soft polyurethane tube 40 to flow and fill the gap 46 along with any other gaps which may exist between it and the shoulder 34, outer surface 36 of the core 16, and the outer surface 54 of the mandrel 50.

U.S. Pat. No. 5,254,107 to Soltesz for a "Catheter Having Extended Braid Reinforced Transitional Tip" discloses an embodiment in col. 4, lines 34–41 wherein an inner tubular plastic layer 22 defines the inner diameter of the catheter, and which extends through the first and second sections 16, 18, but not through third tip section 20. Inner tubular layer 22 may be made of PTFE. A braided stainless steel fiber tubular member 24 surrounds inner plastic layer 22.

In the commonly owned, copending application of Brin et al. for "Improved Method of Catheter Segment Attachment" U.S. application Ser. No. 08/236,766 the distal end of the catheter consists of three segments, the transition tubing which is attached to the shaft, the soft tip tubing which is attached to the transition tubing, and the "plug" tubing which is attached to the soft tip tubing for ease of handling during manufacture and into which a support mandrel is inserted. All three segments are surrounded by a tube of heat shrink. The heat source acts upon the transition tubing with the heat being propagated to the soft tip tubing. After assembly, the plug tubing and part of the soft tip tubing are trimmed off. The catheter shaft is comprised principally of three layers: a lubricous TEFLON® liner, a composite layer of wire braid and polymer, and an outer jacket polymer. The wire braid and TEFLON® liner do not extend into the transition tubing or into the soft tip tubing.

An object of the invention is to create a guiding catheter soft tip with wall thickness less than 0.3 mm which provides improved bond strength to the catheter shaft joints, and in particular, the joint between the soft tip segment and the segment proximal to the soft tip.

Another object of the invention is to provide a lubricous inner lumen throughout the catheter body including throughout the soft tip while shielding the lubricous liner from contact with the vessel wall and while maintaining a curved contour at the distal end.

Another object of the invention is to minimize the length of the unreinforced section of the soft tip to avoid devices snagging during deployment.

SUMMARY OF THE INVENTION

The present invention comprises a catheter and method of manufacture. The catheter includes an elongated core having a unitary lubricous liner and a reinforcement means. The lubricous liner defines at least one lumen. The lubricous liner has the reinforcement means over the its outer diameter and fused to the lubricous liner. The reinforcement means terminates proximal to the distal end of the lubricous liner. The catheter also has an elongated shaft tube which defines a shaft tube lumen. The shaft tube lumen is sized to receive the core, the core which extends longitudinally through the shaft tube lumen. The shaft tube is fused to the core. The catheter also has an elongated transition tube which defines a transition tube lumen. The transition tube lumen is sized to receive the core which extends longitudinally through the transition tube lumen. The distal end of the shaft tube is fused to the proximal end of the transition tube. The transition tube is made of softer material than the shaft tube and is fused to the core. The catheter further includes an elongated tip tube made of softer material then the transition tube. The tip tube defines a tip tube lumen sized to receive the core which extends longitudinally throughout the tip tube lumen. The distal end of the transition tube is fused to the proximal end of the tip tube. The tip tube is fused to the core distal to the distal end of the reinforcement means, the distal end of the tip tube forming a rounded edge which overlaps the distal end of the lubricous liner by about 0.5 mm such that the distal end of the lubricous liner is not exposed.

DETAILED DESCRIPTION OF THE PREFERRED EMBODIMENTS

The present invention addresses the problem created by the trend toward catheters with larger inside diameters and softer distal tip segments. Soft tip guiding catheters are desirable because the gentle ostial engagement is less traumatic. Soft tips provide a coaxial fit in all anatomies to allow for improved device delivery by maintaining a rounded tip shape which adapts to different ostial take-offs. Larger lumens are desirable because they permit more dye flow and offer more device delivery options. The trend toward catheters with larger inside diameters and softer distal tip segments results in a substantially weaker bond between the soft tip and the distal end of the catheter shaft due to thin catheter shaft walls of less than 0.3 mm and to the lower tensile strength of the softer tip materials. Applicants address the problem of bond strength between segments and that of achieving greater lumen lubricity by extending a unitary liner throughout the shaft, transition tubing and soft tip segments, the liner being made of a fluoropolymer such as TEFLON® from E. I. Du Pont de Nemours & Company, Wilmington, Del. TEFLON® which is a form of polytetrafluoroethylene (PTFE) To maintain a soft tip, the TEFLON® is shielded from contact with the vessel wall by using heat shrink tubing in a heating process to draw the distal end of the soft tip material over the exposed TEFLON® liner.

Figure 1:
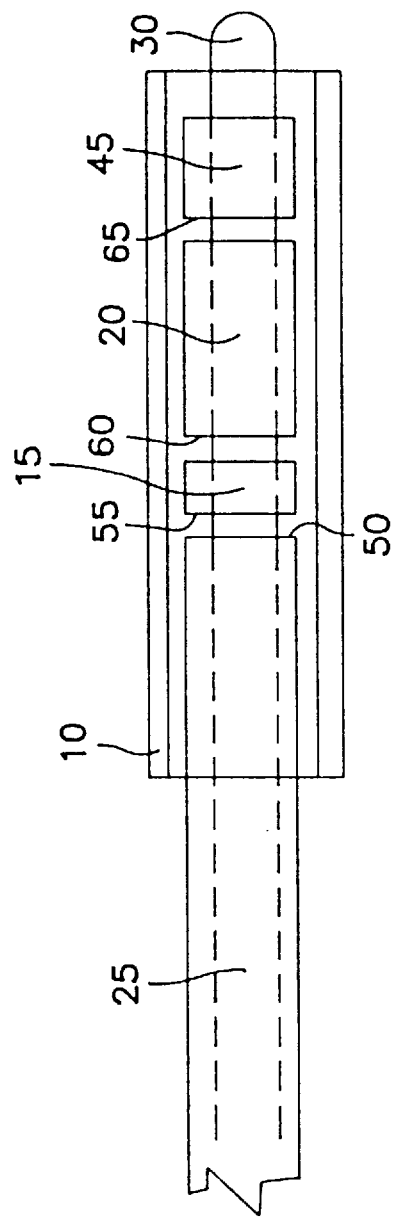
FIG. 1 is the preassembly plan view of the distal end of a guiding catheter prior to the outer jacket molding process.
Figure 2:
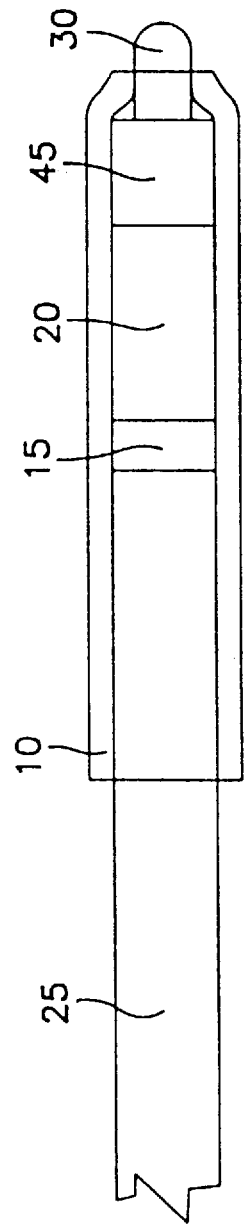
FIG. 2 is the molded assembly of FIG. 1.
Figure 3:
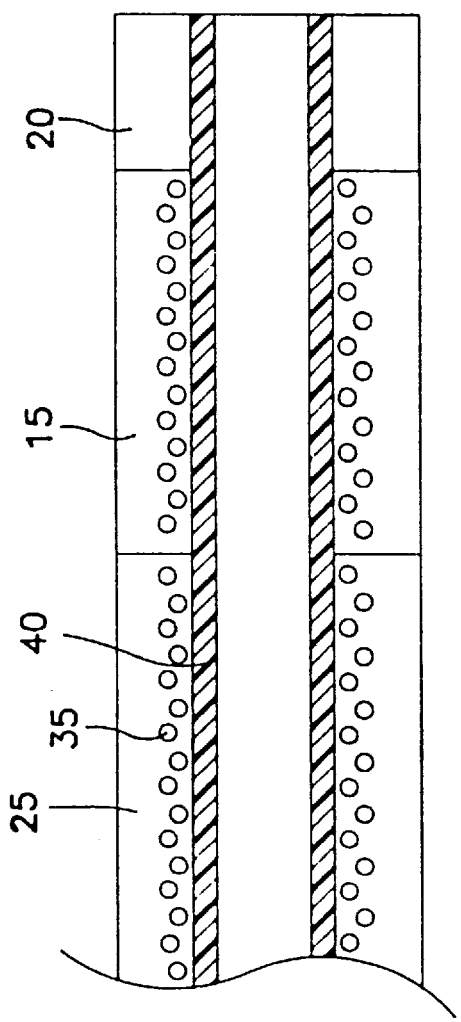
FIG. 3 is the is a cross-sectional view of the distal tip of the molded assembly of FIG. 2.
Figure 4:
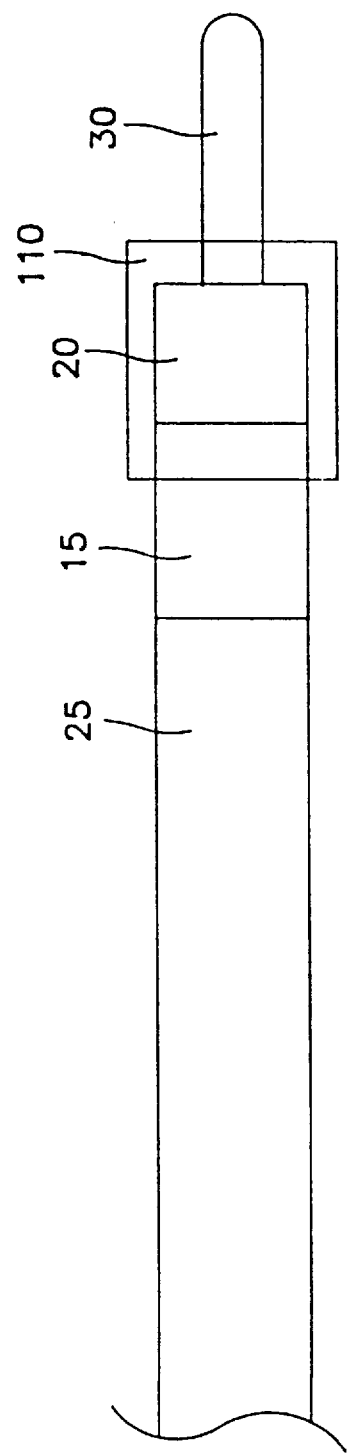
FIG. 4 is the plan view of the distal end of a guiding catheter prior to the soft tip formation process.
Figure 5:
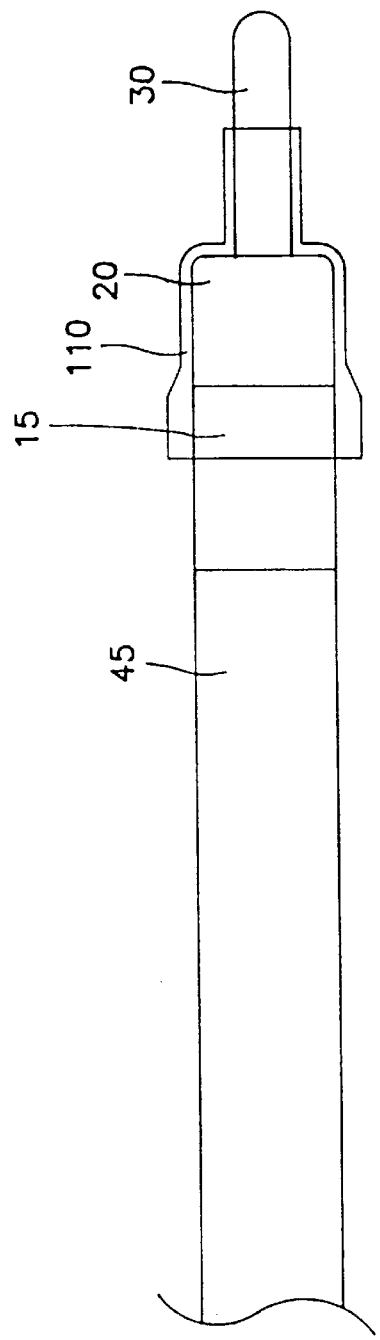
FIG. 5 is the molded assembly of FIG. 4.
Figure 6:
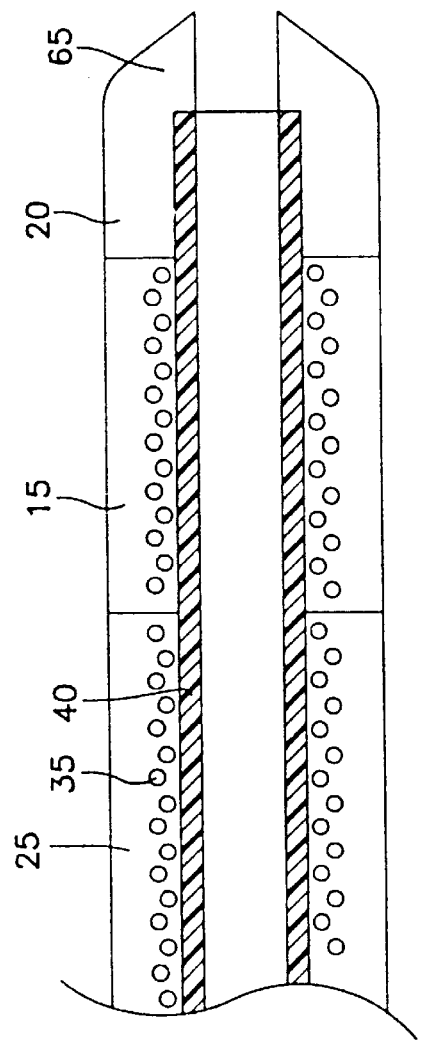
FIG. 6 is a cross-sectional view of the distal tip of the molded assembly of FIG. 5.

Manufacturing applicant's thin wall guiding catheter consists of two major processes, outer jacket molding and soft tip formation. FIG. 1–3, represent applicant's assembly for molding the outer jacket to the braided TEFLON® core material. FIGS. 4–6 represent applicant's assembly for forming the soft tip.

Referring to FIG. 3 which depicts the molded assembly, the shaft of the thin wall guiding catheter for outer jacket molding is assembled as follows. Slide the TEFLON® liner 40 over a stainless steel mandrel 30 (not shown in FIG. 3). The mandrel 30 may optionally be TEFLON® coated. Next, braid wire 35 over the TEFLON® liner 40. The mandrel 30 has an outer diameter of approximately 0.001 inch less than the inner diameter of the TEFLON® liner 40. The mandrel 30 is used for support. TEFLON® beading could be alternatively used for support. After the catheter shaft is assembled, the support will be removed. The TEFLON® liner 40 provides a lubricous surface which aids device delivery by providing a low friction interface. This is especially important for the smooth passage of large, non-balloon devices which may not conform as readily to guiding catheter curves. The TEFLON® 40 enhances device delivery with less device "capture" while ensuring circumferential integrity.

Wire 35 is braided by means of a conventional braiding machine over the TEFLON® liner 40 as shown in FIG. 3. The wire braid 35 is advantageous because it reinforces and supports the large lumen for thin wall guiding catheters. The wire braid 35 is a 16 strand stainless steel braid which runs the length of the catheter and is trimmed a few millimeters proximal to the distal end of the TEFLON® liner 40. The distal end of the wire braid 35 is then adhesively bonded to the TEFLON® liner 40. Those skilled in the art would recognize that other reinforcement means could be used, such as carbon fibers.

The catheter shaft comprises a plurality of segments overlying the wire braid 35 and TEFLON® liner 40. These segments, the 72D shaft tubing 25, the 55D transition tubing 15, the 35D soft tip tubing 20 and the 72D plug tubing 45 are made from PEBAX®. Although other polymers can be found in a suitable durometer range, PEBAX®, a polyether block amide copolymer obtainable from the Elf Atochem Corporation, Philadelphia, Pa., is preferable in catheter design because it is an elastomer, has low moisture absorbance, offers long term stability of material properties, provides high tensile strength and can be processed at temperatures in the 400 degree F. range as required by commonly available extrusion equipment. The segments are abutted as follows.

The shaft tubing 25 is made from PEBAX® in the hardness range of Shore durometer D65–D75 and preferably 72D. The transition tube 15 may have a hardness range of Shore durometer 50D–60D and preferably 55D. Taper the end of the 72D Pebax® shaft tubing 25 using an outside taper cutting tool. Cut a Shore 55D Pebax® transition tube 15 to 3.7 cm in length and taper the end using an inside taper cutting tool. The 3.7 cm length was chosen from an acceptable range of 2 cm to 18 cm based on anatomical considerations, as 4 cm is the average width of the aortic root. Slide the untapered end of the Shore 72D shaft tubing over the braided TEFLON® liner 40 from its distal end. Next slide the 55D transition tubing 15 onto the mandrel 30 and over the braided TEFLON® liner 40 from its distal end such that the tapered end of the 55D transition tubing 15 mates with the tapered end of the 72D shaft tubing. The 72D shaft tubing 25 and 55D transition tubing 15 can be tapered because the materials are stiff enough to retain their shape when melted. The material at the joint will blend better when the mating ends are tapered yielding better bond strength than would an abutted end as there is greater surface area over which to blend the materials. The 55D transition tubing 15 may have a wall thickness of 0.013 inches (0.033 cm) and an inner diameter ranging from a minimum of 0.078 inches for 6F to a maximum of 0.126 inches for 10F. The wire braid 35 extends through the 55D transition tubing 15 to offer better kink resistance and ends preferably at approximately the proximal end of the 35D soft tip tubing 20 to permit maximum flexibility in the soft tip 20. The wire braid 35 can stop from 2–3 mm proximal to the 35D soft tip and still provide sufficient reinforcement but should not extend more than ⅓ of the length of the soft tip 20 into the proximal end of 35D soft tip 20 to provide optimal soft tip 20 flexibility. At least one inch of the mandrel 30 should extend beyond the distal end of the 35D tip tube 20 for ease of handling.

A softer durometer material is used for the soft tip 20 than for the transition tubing 15 to give the distal end more flexibility; this aids in tip placement. The soft tip 20 may be in the range of Shore 25D to 40D and preferably 35D. The 35D tip tube 20 can be made of Pebax®. The 35D tip tube 20 preferably has a length of approximately 1 cm prior to trimming and a wall thickness of 0.013 inches (0.33 cm) and an inner diameter ranging from a minimum of 0.078 inches for 6F to a maximum of 0.126 inches for 10F. The 1 cm length was chosen for handling convenience during the trimming process. Because the TEFLON® liner 40 extends throughout all three segments (the 72D shaft tubing 25, the 55D transition tubing 15 and the 35D soft tip tubing 20) lubricity is improved and device delivery enhanced. Furthermore, the unitary TEFLON® liner 40 extending throughout the shaft improves joint strength between the 72D shaft tubing 25 and the 55D transition tubing 15 as well as between the 55D transition tubing 15 and the 35D soft tip tubing 20.

Slide a Shore 72D Durometer plug tube 45 of approximately 1 cm onto the distal end of the mandrel 30 until it butts against the distal edge of the 35D soft tip tubing. The plug tube 45 can be made of Pebax®. Leave approximately 15.2 cm or 6 inches of mandrel 30 extending distally beyond the assembly for handling convenience.

Slide a segment of TEFLON® fluorinated ethylene propylene (FEP) heat shrink tubing 10 over the entire assembly with approximately 1 cm of heat shrink extending beyond the distal end of the 72D plug tube 45 and over the mandrel 30. Heat shrink tubing such as that from Zeus Industrial can be used. Ensure that the joint between the 55D transition tubing 15 and the 35D soft tip tubing 20 is approximately 15.9 cm from the distal end of the mandrel 30 for handling convenience.

The outer jacket is molded when the heat shrink 10 is heated by any suitable means to fuse the segments. For example, radiant heating or conduction heating can be used. Heat shrink tubing 10 contraction, when coupled with heating the tip materials causes them to expand, resulting in the materials blending and flowing into one another. A lap joint between the materials is produced. Those skilled in the art would recognize that different time and temperature combinations would be suitable as time and temperature vary inversely.

To achieve bonding, the time and temperature selected must be sufficient to render the materials flowable. Temperatures which are too high will result in a brittle product. Temperatures which are too low will result in improper fusion. A suitable convection oven temperature for outer jacket molding includes 185 degrees centigrade. This temperature should be maintained for approximately 7 to 8 minutes depending on the size catheter being molded. Those skilled in the art would recognize that different time and temperature combinations would be suitable as time and temperature vary inversely. Referring to FIG. 2, the heat source causes the catheter shaft tubing 25, the transition tubing 15, the soft tip tubing 20 and the plug tubing 45 to become flowable while the heat shrink 10 contracts both radially and longitudinally thereby colliding all segments. This results in a lap joint between each segment.

The heat shrink tubing 10 is removed with a razor blade and the molded tip assembly is cut to length. The distal end is trimmed back to a point within the 35D soft tip tubing to result in a tip length of 2.5 mm distal to the 55D transition tubing 15. Lengths that are much longer are undesirable because the soft tip 20 is not structurally rigid and may fold back upon itself and cause difficulty with device passage. The mandrel 30 is removed from the inside of the now bonded assembly. FIG. 3 shows the enlarged longitudinal cross section of the distal end portion of the molded assembly of FIG. 2.

After outer jacket molding, the soft tip 20 is formed. Extending the TEFLON® liner 40 to the distal end of the soft tip tubing improves lubricity. The unitary liner also improves joint strength between the 35D soft tip 20 and the 55D transition tubing 15 but results in a tip that is too sharp. To remedy this, a soft tip 20 tapered distal edge which overlaps and shields the TEFLON® liner 40 and can be created as follows to blunt the sharp TEFLON® liner 40. See FIG. 4. Taking the assembly from the outer jacket molding process, insert a mandrel 30 into the distal end of the assembly such that at least 1 inch protrudes from the distal tip of the assembly. Apply approximately 2 inches of heat shrink tubing 110 over the distal end of the assembly such that the heat shrink 110 extends one-half to one centimeter beyond the proximal and distal ends of the soft tip 20 material as seen in FIG. 4. Next insert the assembly (until the soft tip 20 material can no longer be seen) into a preheated forming die, as for example, a hot block consisting of a brass cylinder with and external band heater. Dwell at a temperature of 400 degrees F. This temperature is maintained for approximately 7 to 8 seconds depending on the size catheter being molded. Those skilled in the art would recognize that different time and temperature combinations would be suitable as time and temperature vary inversely. Remove the assembly from the forming die. The heat shrink 110 will have contracted about the soft tip 20 as seen in FIG. 5. After the assembly has cooled for at least 10 seconds, remove the heat shrink tubing 110. Remove the supporting mandrel 30. As seen in FIG. 6, the contraction of the heat shrink 110 will have caused the 35D soft tip 20 material to flow and draw the distal end of the 35D soft tip 20 approximately 0.5 mm over the distal end of the TEFLON® liner 40, thereby covering the exposed TEFLON® liner 40 by creating a somewhat radiused, overhanging edge 65.

Applicants reinforced soft tip 20 with an unreinforced rounded edge 65 is advantageous. A rounded edge 65 shielding the exposed TEFLON® liner 40 reduces trauma in body cavities. It is common to deliver such devices as balloon catheters, stents or atherectomy devices through guiding catheters. Having a short unreinforced soft tip edge 65 of 0.5 mm is advantageous because it diminishes the likelihood of devices snagging during device delivery. Soft tips on guide catheters deflect easily, especially if they are unreinforced. Unreinforced soft tips of two mm or more increase the likelihood of devices snagging during delivery. Unreinforced soft tips of less than 1 mm reduce the likelihood of a device snagging. Applicant's soft tip 20 having the TEFLON® liner 40 throughout the soft tip 20 provides increased stiffness which further avoids devices snagging during deployment.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 10 | Heat Shrink Tubing |
| 15 | 55D Transition Tubing |
| 20 | 35D Soft Tip Tubing |
| 25 | 72D Shaft Tubing |
| 30 | Mandrel |
| 35 | Wire Braid |
| 40 | TEFLON ® Liner |
| 45 | 72D Plug Tube |
| 50 | Shaft Tube Lumen |
| 55 | Transition Tube Lumen |
| 60 | Tip Tube Lumen |
| 65 | Rounded Edge |
| 110 | Heat Shrink Tubing |

What is claimed is:

1. A method of manufacturing a catheter comprising the steps of:

providing a catheter subassembly having a core comprising a lubricious liner and a reinforcement means, the lubricious liner having a distal end, an outer diameter and a proximal end, the lubricious liner defining at least one lumen, the lubricious liner having the reinforcement means over the outer diameter and fused to the lubricious liner, the reinforcement means terminating proximal to the distal end of the lubricious liner;

placing an elongated shaft tube over the proximal end of the core;

placing an elongated transition tube of softer material than the shaft tube over the distal end of the core and abutting the distal end of the shaft tube to the proximal end of the transition tube;

placing an elongated tip tube of softer material than the transition tube over the distal end of the core and abutting the distal end of the transition tube to the proximal end of the tip tube such that the distal end of the reinforcement means ends approximately at the proximal end of the tip tube;

placing a first tube of heat shrink over at least a portion of the shaft tube, transition tube and tip tube;

heating the first heat shrink to fuse the core to the shaft tube, to fuse the transition tube and tip tube, to fuse the distal end of the shaft tube to the proximal end of the transition tube and to fuse the distal end of the transition tube to the proximal end of the tip tube;

removing the first heat shrink from the shaft tube, transition tube, and tip tube;

trimming off a portion of the soft tip tubing;

placing a second tube of heat shrink over the tip tube such that the heat shrink extends beyond the distal end and beyond the proximal end of the tip tube;

applying heat to the tip tube causing the tip material to flow and the second heat shrink to draw the distal end of the tip tube over the distal end of the lubricious liner forming a unitary rounded edge covering the lubricious liner; and removing the second heat shrink from the tip tube, thus completing the catheter manufacture.

2. The method of claim 1 wherein the shaft tube distal end and the transition tube proximal end have complimentary tapers.

3. The method of claim 1 wherein the tip tube has a length of approximately 2.5 mm.

4. The method of claim 1 wherein the transition tube has a length of approximately 3.7 cm.

5. The method of claim 1 wherein the distal end of the reinforcement means ends not less then approximately 2–3 mm proximal to the proximal end of the tip tube and not more then approximately ⅓ of the length of the tip tube from the proximal end of the tip tube.

6. The method of claim 1 wherein the reinforcement means comprises a wire braid.

7. The method of claim 1 wherein the transition tube is made from a polymer material exhibiting a hardness in the range of Shore durometer 50D to 60D.

8. The method of claim 1 wherein the tip tube is made from a polymer material exhibiting a hardness in the range of Shore durometer 25D–40D.

9. The method of claim 1 wherein the rounded edge extends approximately 0.5 mm distally beyond the lubricious liner.

10. The method of claim 1 wherein the rounded edge extends approximately 0.5 mm distally beyond the lubricious liner.

11. A method of reshaping a catheter tip comprising the steps of:

providing a catheter having a distal end and a lubricious liner extending longitudinally throughout the catheter, the lubricious liner defining at least one lumen;

placing a tube of heat shrink over the distal end of the catheter such that the heat extends beyond the distal end of the catheter;

applying heat to the heat shrink causing the material at the distal end of the catheter to flow and the heat shrink to draw the distal end of the catheter over the distal end of the lubricious liner thereby forming a unitary rounded edge covering the lubricious liner; and removing the heat shrink from the distal end of the catheter, such that a reshaped tip is formed.

12. The method of claim 11 wherein the rounded edge extends approximately 0.5 mm distally beyond the lubricious liner.

* * * * *